United States Patent [19]

Samejima et al.

[11] Patent Number: 4,486,471

[45] Date of Patent: Dec. 4, 1984

[54] PROCESS FOR PREPARING ETHYLCELLULOSE MICROCAPSULES

[75] Inventors: Masayoshi Samejima, Minoh; Goichi Hirata, Yawata; Yoshiyuki Koida, Katano; Akira Kida, Settsu, all of Japan

[73] Assignee: Tanabe Seiyaku Co., Ltd., Osaka, Japan

[21] Appl. No.: 375,046

[22] Filed: May 5, 1982

[30] Foreign Application Priority Data

May 29, 1981 [JP] Japan ................. 56-82728

[51] Int. Cl.³ ............... A61K 9/52; A61K 9/62; B01J 13/02
[52] U.S. Cl. ................. 427/213.3; 424/19; 424/33; 424/35; 428/402.24
[58] Field of Search .......... 427/213.3; 428/402.24; 424/33, 35, 19

[56] References Cited

U.S. PATENT DOCUMENTS

| | | | |
|---|---|---|---|
| 3,415,758 | 12/1968 | Powell et al. | 428/402.24 X |
| 3,531,418 | 9/1970 | Fanger et al. | 427/213.3 |
| 3,859,228 | 1/1975 | Morishita et al. | 428/402.24 X |
| 3,960,757 | 6/1976 | Morishita et al. | 428/402.24 X |

*Primary Examiner*—Richard D. Lovering
*Attorney, Agent, or Firm*—Jordan B. Bierman

[57] ABSTRACT

Pharmaceutically active compound-containing microcapsules the coating walls of which consist essentially of ethylcellulose and a water-insoluble, acid-soluble polymer material are disclosed. A method of preparing said microcapsules is also disclosed.

20 Claims, No Drawings

PROCESS FOR PREPARING ETHYLCELLULOSE MICROCAPSULES

This invention relates to novel ethylcellulose microcapsules and a process for preparing same.

It is known that ethylcellulose microcapsules are prepared by taking advantage of the liquid-liquid phase separation of ethylcellulose in cyclohexane. For example, Japanese Patent Publication (examined) Nos. 528/1967, 11399/1969 and 30136/1975 disclose that said microcapsules are obtained by preparing a hot solution in cyclohexane of ethylcellulose and a phase-separation-inducing agent (e.g., butyl rubber, polybutadiene, polyethylene, polyisobutylene), dispersing particles of a core material in the solution, cooling the dispersion until the ethylcellulose separates out from the dispersion to form a liquid phase depositing on and around the particles of the core material, and then recovering the so formed microcapsules therefrom. Further, U.S. Pat. No. 3,531,418 discloses a method of preparing ethylcellulose microcapsules without using a phase-separation-inducing agent, i.e., direct flocculation of ethylcellulose by change of temperature. According to the known methods, however, it is difficult to obtain microcapsules which show rapid release of a pharmaceutically active compound in the stomach because the compact wall structure of ethylcellulose retards the release of the pharmaceutically active compound.

The present invention provides for pharmaceutically active compound-containing ethylcellulose microcapsules which show rapid release of said pharmaceutically active compound in stomach or gastric juice. The present invention also provides for pharmaceutically active compound-containing microcapsules the coating walls of which consist essentially of ethylcellulose and a water-insoluble, acid-soluble polymer material. The present invention further provides a method for preparing such ethylcellulose microcapsules.

According to the present invention, the pharmaceutically active compound-containing microcapsules whose coating walls consist essentially of ehylcellulose and a water-insoluble, acid-soluble polymer material can be prepared by the steps of:

(i) dissolving ethylcellulose in a solvent, (ii) dispersing particles of a pharmaceutically active compound (core material) in the solution, (iii) cooling the dispersion in the presence of a water-insoluble, acid-soluble polymer material until the ethylcellulose separates out from the dispersion to form coating walls on and around the particles of said core material, and then, (iv) recovering the thus-formed microcapsules therefrom.

A wide variety of polymer materials soluble in water at a pH of not higher than 5 can be used as the water-insoluble, acid-soluble polymer material of the present invention. Examples of such polymer material include dialkylaminoalkyl-cellulose (e.g., diethylaminomethylcellulose), benzylaminoalkyl-cellulose (e.g., benzylaminomethylcellulose), carboxyalkyl(benzylamino)cellulose (e.g., carboxymethyl(benzylamino)cellulose), dialkylaminoacetate.cellulose.acetate (e.g., diethylaminoacetate.cellulose.acetate), cellulose.acetate.dialkylamino.hydroxyalkyl ether (e.g., cellulose.acetate.N,N-di-n-butylamino.hydroxypropyl ether), piperidyl.alkyl.hydroxyalkylcellulose (e.g., piperidyl.ethyl.hydroxypropylcellulose, piperidyl.ethyl.hydroxyethylcellulose), carboxyalkyl.piperidyl.starch (e.g., carboxymethyl.piperidyl.starch), poly-dialkylaminoalkylstyrene (e.g., poly-diethylaminomethylstyrene), poly-vinylacetacetal.dialkylaminoacetate (e.g., poly-vinylacetacetal.dimethylaminoacetate, poly-vinylacetacetal.diethylaminoacetate), 2-(p-vinylphenyl)glycine.vinyl acetate copolymer, N-vinylglycine.styrene copolymer, a copolymer of (A) dialkylaminoalkyl methacrylate and (B) one or two alkyl methacrylates (e.g., dimethylaminoethyl methacrylate.methyl methacrylate copolymer, butyl methacrylate.2-dimethylaminoethyl methacrylate-methyl methacrylate copolymer), a copolymer of (A) 2-alkyl-5-vinylpyridine, (B) alkyl acrylate or acrylonitrile and (C) methacrylic acid (e.g., 2-methyl-5-vinylpyridine.methyl acrylate.methacrylic acid copolymer, 2-methyl-5-vinylpyridine.acrylonitrile.methacrylic acid copolymer), a copolymer of 2-vinyl-5-alkylpyridine and styrene (e.g., 2-vinyl-5-ethylpyridine.styrene copolymer), and a copolymer of 2-vinylpyridine and alkyl methacrylate (e.g., 2-vinylpyridine.methyl methacrylate copolymer). Preferred examples of such polymer material include diethylaminomethylcellulose, benzylaminomethylcellulose, carboxymethyl(benzylamino)cellulose, diethylaminoacetate.cellulose.acetate, cellulose.acetate.N,N-di-n-butylamino.hydroxypropyl ether, piperidyl.ethyl.hydroxypropylcellulose, piperidyl.ethyl.hydroxyethylcellulose, carboxymethyl.piperidyl.starch, poly-diethylaminomethylstyrene, poly-vinylacetacetal.diethylaminoacetate, 2-(p-vinylphenyl)glycine.vinyl acetate copolymer, N-vinylglycine.styrene copolymer, dimethylaminoethyl methacrylate.methyl methacrylate copolymer, butyl methacrylate-2-dimethyl-aminoethyl methacrylate.methyl methacrylate copolymer, 2-methyl-5-vinylpyridine.methyl acrylate.methacrylic acid copolymer, 2-methyl-5-vinylpyridine-acrylonitrile.methacrylic acid copolymer, 2-vinyl-5-ethylpyridine.styrene copolymer and 2-vinylpyridine.methyl methacrylate copolymer. More preferred examples of the polymer material include 2-methyl-5-vinylpyridine.methyl acrylate.methacrylic acid copolymer, poly-vinylacetacetal.diethylaminoacetate, dimethylaminoethyl methacrylate.methyl acrylate copolymer and cellulose.acetate.N,N-di-n-butylamino.hydroxypropyl ether.

In making the microcapsules of the present invention it is preferred that these polymer materials have a particle diameter of not more than one-tenth that of the core material, especially a particly size of not more than $50\mu$, more especially of not more than $20\mu$. It is also preferred that these polymer materials are used in an amount of 0.1 to 20 grams, especially 0.5 to 10 grams, per gram of ethylcellulose used.

On the other hand, ethylcellulose having an ethoxy content of 47 to 55 W/W % is preferably used as the wall-forming material of the present invention. It is preferred that the viscosity of said ethylcellulose when measured at 25° C. with respect to a 5 W/W % solution of it in toluene-ethanol (4:1) is within the range of 3 to 500 cP, especially 20 to 200 cP. It is also preferred that said ethylcellulose is used in an amount of 0.05 to 5 grams, especially 0.1 to 1 gram, per gram of the core material used.

Any solvents which dissolve ethylcellulose at a temperature of 70° to 80° C. and which does not dissolve the core material and the water-insoluble, acid-soluble polymer material can be used as the solvent of the invention. Examples of such solvent are cyclohexane, a mixture of cyclohexane and n-hexane, and the like. Especially, it is preferred to use cyclohexane as the solvent.

Any pharmaceutically active compounds (or medicaments) can be used as the core material to be microencapsulated in the present invention. Such pharmaceutically active compound or medicament to be microencapsulated may be either solid, gel or semi-solid. In order to prepare a homogenous dispersion at the microencapsulation step, it is preferred that said pharmaceutically active compound or medicament has a particle size of 30 to 1000μ, especially 50 to 500μ. Eligible for microencapsulation as solids are particles of materials such as, for example, vitamines (e.g., ascorbic acid), amino acids (e.g., potassium aspartate, magnesium aspartate), minerals (e.g., potassium chloride), antimicrobial agents (e.g., benzylpenicillin potassium salt, sulfomethizole), anti-tumor agents (e.g., 5-fluorouracil, bleomycin hydrochloride), metabolic agents (e.g., glutathion), cardiovascular agents (e.g., dilthiazem hydrochloride), analgesics (e.g., acetylsalicylic acid), anti-histaminics (e.g., diphenhydramine hydrochloride), neuropsycotropic agents (e.g., calcium N-(γ,γ-dihydroxy-β,β-dimethylbutyryl)-γ-aminobutyrate), agents affecting digestive organs (e.g., methylmethionine sulfonium chloride, 1,1-dimethyl-5-methoxy-3-(dithien-2-yl-methylene)-piperidinium bromide, precipitated calcium carbonate, 1-(3,4,5-trimethoxybenzoyloxy)-2-dimethylamino-2-phenylbutane maleate), agents affecting respiratory organs (e.g., tri-methoquinol hydrochloride), and so forth. Also eligible for microencapsulation as semi-solids are, for example, slurries such as a slurry composed of 30 W/W % of sodium polyacrylate, 40 W/W % of water and 30 W/W % of 5-fluorouracil And pharmaceutically active compounds in the form of "gel" which can be microencapsulated include, for example, dextran gel having a medicament (e.g., methylmethionine sulfonium chloride) adsorbed therein, formalin-treated gelatin gel having a medicament (e.g., sulfamethomidine) dispersed therein, and so forth.

Further, the core material to be microencapsulated may contain a water-soluble organic acid. Said organic acid serves to accelerate the release of the pharmaceutically active compound from microcapsules. Examples of such organic acid include hydroxy-lower alkane-dicarboxylic acid (e.g., malic acid, tartaric acid), hydroxy-lower alkane-tricarboxylic acid (e.g., citric acid), lower alkane-dicarboxylic acid (e.g., malonic acid, succinic acid) and lower alkene-dicarboxylic acid(e.g., maleic acid, fumaric acid). It is preferred that said acid has a particle size of not more than 30μ. It is also preferred that the amount of said acid in the core material is within the range of one to 90 W/W %, especially 10 to 80 W/W %. The organic acid-containing core material may be prepared by granulating a mixture of the core material and the organic acid by conventional means (e.g., wet-granulation method, dry-granulation method), and the particle size of the organic acid-containing core material should be preferably within a range of 30 to 1,000μ.

In making the microcapsules of a pharmaceutically active compounds according to the present invention, it is preferred to dissolve ethylcellulose in a solvent such as those mentioned above, and then dispersing the particles of a pharmaceuticcally active compound (core material) to the solution under stirring. In this case, it is preferred to dissolve ethylcellulose at a temperature of 70° to 80° C. Further, it is also preferred to dissolve ethylcellulose at a concentration of 0.5 to 10 W/W %, especially one to 5 W/W %.

When the above-mentioned dispersion is cooled in the presence of the water-insoluble, acid-soluble polymer material, ethylcellulose separates out in the form of "gel" from the dispersion by flocculation thereof to form coating walls of and around particles of the core material and at the same time said water-insoluble, acid-soluble polymer material is incorporated into the coating walls of the embryonic microcapsules. It is preferred to cool the dispersion at a rate of 0.05° to 4° C., especially 0.1° to 2° C., per minute.

The water-insoluble, acid-soluble polymer material may be added to the dispersion either before cooling said dispersion or during the cooling step. Especially, it is preferred that the polymer material is added to the dispersion at the stage where coating walls of ethylcellulose in the form of "gel" is formed on and around the particles of the pharmaceutically active compound (core material) and the thus-formed coating walls have a viscosity of 0.1 to 50 P, especially 1 to 10 P. More specifically, since the coating walls having a viscosity of the above-mentioned range is formed on and around the core material by cooling the dispersion to 55° to 75° C., especially 60° to 70° C., it is preferred that the polymer material is added to the dispersion when cooled to said temperature. When the dispersion is further cooled to a temperature not higher than 40° C. (e.g., 30° to 20° C.), the thus-formed embryonic microcapsules are shrunken and become solid by solvent loss from the coating walls, thus giving stable ethylcellulose microcapsules.

The microcapsules thus obtained may be recovered by conventional manners such as, for example, decantation, centrifugation, filtration and so forth. Further, if required, the ethylcellulose microcapsules may be washed with a suitable solvent (e.g., cyclohexane, petroleum-ether, n-hexane) and then dried by conventional manners (e.g., hot-air drying method).

Further, in carrying out the phase-separation of ethylcellulose, a phase-separation-inducing agent, an organopolysiloxane and a surfactant may be used in combination with ethylcellulose. Suitable examples of the phase-separation-inducing agent include polyethylene, butyl rubber, polyisobutylene and polybutadiene. Dimethylpolysiloxane and methylphenylpolysiloxane are suitable as the organopolysiloxane. Further, the surfactants which can be used in the present invention include, for example, an ester of $C_{12-18}$ fatty acid with sorbitan (e.g., sorbitan monolaurate, sorbitan sesquilaurate, sorbitan trilaurate, sorbitan monooleate), an ester of $C_{6-18}$ fatty acid with glycerin (e.g., glycerin monocaprylate, glycerin monolaurate, glycerin monooleate), a phospholipid (e.g., soybean phospholipid) and calcium stearoyl-2-lactylate. It is preferred that said phase-separation-inducing agent, organopolysiloxane and surfactant are added to the ethylcellulose solution prior to dispersing the core material in said solution. Suitable concentration of the phase-separation-inducing agent, the organopolysiloxane and the surfactant in the ethylcellulose solution is 0.1 to 10 W/V %, 0.01 to 10 W/V % and 0.003 to 10 W/V %, respectively.

Pharmaceutically active compound-containing microcapsules the capsule walls of which are composed of ethylcellulose and a water-insoluble, acid-soluble polymer material are obtained by any one of the above-mentioned operations. Preferred amount of the polymer material which is contained or incorporated in the coating walls of ethylcellulose is 0.2 to 20 grams, especially 1 to 10 grams, per gram of ethylcellulose.

The pharmaceutically active compound-containing microcapsules of the present invention thus obtained show rapid release of said pharmaceutically active compound (core material) in stomach or other gastric organs because the water-insoluble, acid-soluble polymer material incorporated or contained in the coating walls of ethylcellulose dissolve swiftly in the presence of hydronium ion, for example, in an acidic solution such as gastric juice. Namely, the coating walls of the microcapsules of the invention when contacted with hydronium ion become porous and permeable to water, and water thus permeated or penetrated into the microcapsules serves to dissolve the core material and release it rapidly from the microcapsules. Moreover, when an organic acid-containing core material is used in the invention, said acid further accelerates the release of a pharmaceutically active compound from the microcapsules because the hydronium ion which said organic acid releases in water induces the dissolution of the polymer material from the interior side of the coating walls and serves to increase the porosity of said coating walls. In the microcapsules of the present invention the release velocity of a pharmaceutically active compound can be controlled by suitable choice of the amount of the polymer material and/or organic acid used. Further, as mentioned above, hydronium ion which the organic acid releases in water makes the coating walls porous enough to release the pharmaceutically active compound in stomach from the microcapsules and, therefore, the microcapsules which are obtained by using an organic acid-containing core material show no substantial retardation in release of a pharmaceutically active compound in stomach even when administered orally to patients suffering from hypoacidity or anacidity.

Practical and presently-preferred embodiments of the present invention are illustratively shown in the following lines. Throughout the specification and claims, the terms "alkyl", "lower alkane" and "lower alkene" should be interpreted as referring to alkyl of one to 4 carbon atoms, lowr alkane of one to 4 carbon atoms and lower alkene of 2 to 4 carbon atoms, respectively.

EXPERIMENT I

Microcapsules containing trimebutine maleate(-chemical name: 1-(3,4,5-trimethoxybenzoyloxy)-2-dimethylamino-2-phenylbutane maleate) were prepared according to the following method. Then, the yield of microcapsules thus obtained, the amount of the active ingredient contained in the microcapsules and the 50% release time (i.e., a period of time which was necessary to release 50% of the active ingredient from the microcapsules) were examined, respectively.

(Method)

(i) Core material:

20 parts (by weight) of an aqueous 15 W/V % methylcellulose solution were added to a mixture of 23 parts (by weight) of trimebutine maleate and 74 parts (by weight) of lactose, and the mixture was granulated and dried in a conventional manner. The granules (particle size: 105–210μ) thus obtained were used as the core material.

(ii) Preparation of microcapsules:

27 g of silicone resin which met the requirements specified in JAPANESE STANDARDS OF FOOD ADDITIVE 4th-Edition [said silicone resin being prepared by dispersing silicon dioxide at a concentration of 3–15 W/W % in dimethylpolysiloxane (viscosity: 100–1,100 cSt at 25° C.)] and 20 g of ethylcellulose (ethoxy content: 48.5 W/W %, viscosity: 100 cP) were dissolved at 80° C. in 700 ml of cyclohexane under stirring. 100 g of the core material were dispersed in the solution, and the dispersion was cooled to about 70° C. under stirring at 400 r.p.m.. Then, a suspension of 2-methyl-5-vinylpyridine.methyl acrylate.methacrylic acid copolymer (molar ratio=2.4:1.9:1; average particle size: 7μ) in 200 ml of cyclohexane containing soybean phospholipid (0.8 g/200 ml) was added to the dispersion, and said dispersion was cooled to room temperature. The microcapsules thus obtained were recovered by filtration, washed with n-hexane and then dried. Said microcapsules were passed through JIS standard sieve (350μ aperture). Trimebutine maleate-containing microcapsules which met the requirements of "Pulvers" specified in THE PHARMACOPOEIA OF JAPAN 9th-Edition were obtained.

(iii) Estimation of release time:

The microcapsules obtained in paragraph (ii) were added to water or a simulated gastric fluid specified in THE PHARMACOPOEIA OF JAPAN 9th-Edition, and the mixture was stirred at 37° C. The amount of the active ingredient released from the microcapsules was examined with the lapse of time, and the 50% release time of the active ingredient was estimated therefrom.

(Results)

The results are shown in the following Table 1.

TABLE 1

| Experiment Nos. | Amount of copolymer used (g) | Yield of microcapsules (g) | Amount of active ingredient contained in microcapsules (%) | 50% release time (minutes) | |
|---|---|---|---|---|---|
| | | | | water | simulated gastric fluid |
| (The methods of the present invention) | | | | | |
| 1. | 30 | 144 | 15.5 | 80 | 17 |
| 2. | 100 | 209 | 10.7 | 87 | 8 |
| 3. | 150 | 265 | 8.5 | 76 | 5 |
| (Control) | | | | | |
| 4. | 0 | 114 | 19.3 | 78 | 37 |

EXPERIMENT II

Microcapsules containing timepidium bromide (chemical name: 1,1-dimethyl-5-methoxy-3-(dithien-2-ylmethylene)-piperidinium bromide) and citric acid were prepared according to the following method. Then, the yield of microcapsules thus obtained, the amount of the active ingredient contained in the microcapsules and the 50% release time (i.e., a period of time which was necessary to release 50% of the active ingredient from the microcapsules) were examined, respectively.

(Method)

(i) Core material:

28 parkts (by weight) of a 25 W/V % solution of poly-vinyl acetate in ethanol were added to a mixture of 23 parts (by weight) of timepidium bromide, 37 parts (by weight) of citric acid and 33 parts (by weight) of lactose, and the mixture was granulated and dried in a conventional manner. The granules (particle size: 105–210μ) thus obtained were used as the core material.

(ii) Preparation of microcapsules:

22.5 g of dimethylpolysiloxane (viscosity: 10,000 cSt at 25° C.) and 25 g of ethylcellulose (ethoxy content: 48.5 W/W %, viscosity: 100 cP) were dissolved at 80° C. in 700 ml of cyclohexane under stirring. 100 g of the core material were dispersed in the solution, and the dispersion was cooled to about 75° C. under stirring at 400 r.p.m.. To the dispersion was added a suspension of 2-methyl-5-vinylpyridine.methyl acrylate.methacrylic acid copolymer (molar ratio=2.4:1.9:1) in 150 ml of cyclohexane containing soybean phospholipid (0.085 g/150 ml). Then, said dispersion was treated in the same manner as described in Experiment I. Timepidium bromide-containing microcapsules which met the requirements of "Pulvers" specified in THE PHARMACOPOEIA OF JAPAN 9th-Edition were thereby obtained as shown in the following Table 2.

TABLE 2

| Experiment Nos. | Amount of copolymer used (g) | Yield of microcapsules (g) | Amount of active ingredient contained in microcapsules (%) |
|---|---|---|---|
| (The method of the present invention) | | | |
| 1. | 125 | 243 | 9.3 |
| (Control) | | | |
| 2. | 0 | 122 | 18.2 |

(iii) Estimation of release time:

The microcapsules obtained in paragraph (ii) were added to water, and the mixture was stirred at 37° C. The amount (%) of the active ingredient released from the microcapsules was examined with the lapse of time, and the 50% release time of the active ingredient were estimated therefrom.

(Results)

The results are shown in the following Table 3.

TABLE 3

| Period of time (minutes) | The amount (%) of the active ingredient released from the microcapsules | |
|---|---|---|
| | Microcapsules of the present invention (the amount of copolymer: 125 g) | Control (the amount of copolymer: 0 g) |
| 10 | 15 | 2 |
| 15 | 28 | 3 |
| 20 | 41 | 7 |
| 30 | 60 | 12 |
| 45 | 76 | 20 |
| 60 | 86 | 28 |
| 90 | 94 | 43 |
| 120 | 98 | 56 |
| 50% release time | 24 minutes | 106 minutes |

EXAMPLE 1

30 g of polyethylene (molecular weight: 7,000) and 25 g of ethylcellulose (ethoxy content: 48.0 W/W %; viscosity: 45 cP) were dissolved at 80° C. in 850 ml of cyclohexane, and 100 g of glutathion having a particle size of 105–210μ were dispersed in the solution. The dispersion was cooled to about 65° C. under stirring at 350 r.p.m.. 150 g of polyvinylacetal diethylaminoacetate (nitrogen content: 2.0 W/W %; average particle size: 10μ) were added gradually to the dispersion, and said dispersion was cooled to room temperature. The microcapsules thus obtained were recovered by filtration, washed with n-hexane, and then dried. Then, said microcapsules were passed through JIS standard sieve (350μ aperture). 265 g of glutathion-containing microcapsules which met the requirements of "Pulvers" specified in THE JAPANESE PHARMACOPOEIA OF JAPAN 9th-Edition were obtained.

| | |
|---|---|
| Amount of glutathion contained in the microcapsules: | 36.4 W/W % |
| 50% release time of glutathion in water (estimated in the same manner as described in Experiment I): | 106 minutes |
| 50% release time of glutathion in a simulated gastric fluid (estimated in the same manner as described in Experiment I): | 17 minutes |

EXAMPLE 2

Microcapsules were prepared in the same manner as described in Example 1 except that 30 g of polyisobutylene (molecular weight: 700,000) and 150 g of dimethylaminoethyl methacrylate.methyl methacrylate copolymer (molar ratio=1:1) (average particle size: 9.6μ) were used instead of polyethylene and polyvinylacetal.diethylaminoacetate. 268 g of glutathion-containing microcapsules which met the requirements of "Pulvers" specified above were obtained.

| | |
|---|---|
| Amount of glutathion contained in the microcapsules: | 36.3 W/W % |
| 50% release time of glutathion in water (estimated in the same manner as described in Experiment I): | 98 minutes |
| 50% release time of glutathion in a simulated gastric fluid (estimated in the same manner as described in Experiment I): | 20 minutes |

EXAMPLE 3

30 g of polyethylene (molecular weight: 7,000) and 25 g of ethylcellulose (ethoxy content: 48.0 W/W %; viscosity: 45 cP) were dissolved at 80° C. in 850 ml of cyclohexane, and 100 g of trimethoquinol hydrochloride (chemical name: 1-1-(3,4,5-trimethoxybenzyl)-6,7-dihydroxy-1,2,3,4-tetrahydroisoquinoline hydrochloride monohydrate) having a particle size of 149–297μ were dispersed in the solution. The dispersion was cooled to about 65° C. under stirring at 350 r.p.m.. 150 g of 2-vinyl-5-ethylpyridine.styrene copolymer (molar ratio=1:1) (average article size: 13μ) were added gradually to the dispersion, and said dispersion was cooled to room temperature. The microcapsules thus obtained are treated in the same manner as described in Example 1, whereby 265 g of trimethoquinol hydrochloride-containing microcapsules which met the requirements of "Pulvers" specified above were obtained.

| | |
|---|---|
| Amount of trimethoquinol hydrochloride contained in the microcapsules: | 36.3 W/W % |
| 50% release time of trimethoquinol hydrochloride in water (estimated in the same manner as described in Experiment I): | 158 minutes |
| 50% release time of trimethoquinol hydrochloride in a simulated gastric fluid (estimated in the same manner | 21 minutes |

-continued as described in Experiment I):

EXAMPLES 4–17

Microcapsules were prepared in the same manner as described in Experiment I except that 100 g of a polymer shown in the following Table 4 were used instead of 2-methyl-5-vinylpyridine.methyl acrylate.methacrylic acid copolymer. Trimebutine maleate-containing microcapsules which met the requirements of "Pulvers" specified above were thereby obtained as shown in Table 4.

TABLE 4

| Example Nos. | Polymers | Yield of microcapsules (g) | (%)*[1] |
|---|---|---|---|
| 4. | diethylaminomethylcellulose | 213 | 97 |
| 5. | benzylaminomethylcellulose | 202 | 92 |
| 6. | carboxymethyl(benzylamino)cellulose | 209 | 95 |
| 7. | diethylaminoacetate.cellulose.acetate | 205 | 93 |
| 8. | cellulose.acetate.N,N—di-n-butylamino.hydroxypropyl ether | 200 | 91 |
| 9. | piperidyl.ethyl.hydroxypropylcellulose | 202 | 92 |
| 10. | piperidyl.ethyl.hydroxyethylcellulose | 205 | 93 |
| 11. | carboxymethyl.piperidyl.starch | 216 | 98 |
| 12. | poly-diethylaminomethylstyrene | 207 | 94 |
| 13. | 2-methyl-5-vinylpyridine.acrylonitrile.methacrylic acid copolymer | 194 | 88 |
| 14. | 2-vinylpyridine.methyl methacrylate copolymer | 200 | 91 |
| 15. | 2-(p-vinylphenyl)glycine.vinyl acetate copolymer | 209 | 95 |
| 16. | N—vinylglycine.styrene copolymer | 202 | 92 |
| 17. | butyl methacrylate.2-dimethylaminoethyl methacrylate.methyl methacrylate copolymer | 203 | 92 |

Note:
*[1]The yield (%) of microcapsules was calculated to the following formula:

$Y = \frac{a}{b} \times Y_{obs}$ a: amount (%) of active ingredient contained in microcapsules
b: amount (grams) of active ingredient used
Yobs: yield (grams) of microcapsules which met the requirements of "Pulvers" specified in THE PHARMACOPOEIA OF JAPAN 9th-Edition.

What we claim is:

1. A method of preparing ethylcellulose microcapsules comprising:
   (i) dissolving ethylcellulose having an ethoxy content of 47 to 55 w/w % in cyclohexane to form a solution,
   (ii) dispersing particles of a pharmaceutically active compound, having a particle size of 30–1000 microns, in said solution to form a dispersion,
   (iii) adding a water-insoluble, acid-soluble polymer material to said dispersion in an amount of 0.1 to 20 grams per gram of said ethylcellulose, and
   (iv) cooling said dispersion containing said polymer material until said ethylcellulose separates therefrom to form coating walls on and around said particles of said pharmaceutically active compound thereby forming microcapsules.

2. A method of preparing ethylcellulose microcapsules comprising:
   (i) dissolving ethylcellulose having a ethoxy content of 47 to 55 w/w % in cyclohexane to form a solution,
   (ii) dispersing particles of a pharmaceutically active compound, having a particle size of 30–1000 microns, in said solution to form a dispersion,
   (iii) cooling said dispersion until coating walls, having a viscosity of 0.1 to 50 P, are formed on and around said particles of said pharmaceutically active compound,
   (iv) adding a water-insoluble, acid-soluble polymer material to said dispersion in an amount of 0.1 to 20 grams per gram of ethylcellulose, and
   (v) further cooling the product of Step (iv) until the resulting embryonic microcapsules shrink and become solid by solvent loss from said coating walls thereby forming microcapsules.

3. A method of preparing ethylcellulose microcapsules comprising:
   (i) dissolving ethylcellulose having an ethoxy content of 47 to 55 w/w % in cyclohexane to form a solution,
   (ii) dispersing particles of a pharmaceutically active compound, having a particle size of 30–1000 microns, in said solution to form a dispersion,
   (iii) adding a water-insoluble, acid-soluble polymer material to said dispersion in an amount of 0.1 to 20 grams per gram of said ethylcellulose,
   (iv) cooling said dispersion containing said polymer material until said ethylcellulose separates therefrom to form coating walls on and around said particles of said pharmaceutically active compound thereby forming microcapsules, and
   (v) recovering said microcapsules.

4. The method according to claim 3, wherein the water-insoluble, acid-soluble polymer material is dialkylaminoalkycellulose, benzylaminoalkylcellulose, carboxyalkyl(benzylamino)cellulose, dialkylaminoacetate.cellulose.acetate, cellulose.acetate.dialkylamino.hydroxyalkyl ether, piperidyl.alkyl.hydroxyalkylcellulose, carboxyalkyl.piperidyl.starch, poly-dialkylaminoalkylstyrene, poly-vinylacetacetal.dialkylaminoacetate, 2-(p-vinylphenyl)glycine.vinyl acetate copolymer, N-vinylglycine.styrene copolymer, a copolymer of (A) dialkylaminoalkyl methacrylate and (B) one or two alkyl methacrylates, a copolymer of (A) 2-alkyl-5-vinylpyridine, (B) alkyl acrylate or acrylonitrile and (C) methacrylic acid, a copolymer of 2-vinyl-5-alkylpyridine and styrene, or a copolymer of 2-vinylpyridine and alkyl methacrylate.

5. The method according to claim 3, wherein the water-insoluble, acid-soluble polymer material is diethylaminomethylcellulose, benzylaminomethylcellulose, carboxymethyl(benzylamino)cellulose, diethylaminoacetate.cellulose.acetate, cellulose.acetate.N,N-di-n-butylamino.hydroxypropyl ether, piperidyl.ethyl.hydroxypropylcellulose, piperidyl.ethyl. hydroxyethylcellulose, carboxymethyl.piperidyl.starch, poly-diethylaminomethylstyrene, poly-vinylacetacetal.diethylaminoacetate, 2-(p-vinylphenyl)glycine.vinyl acetate copolymer, N-vinylglycine.styrene copolymer, dimethylaminoethyl methacrylate.methyl methacrylate copolymer, butyl methacrylate.2-dimethylaminoethyl methacrylate.methyl methacrylate copolymer, 2-methyl-5-vinylpyridine.methyl acrylate.methacrylic acid copolymer, 2-methyl- 5-vinylpyridine.acrylonitrile.methacrylic acid copolymer, 2-vinyl-5-ethylpyridine.styrene copolymer or 2-vinylpyridine.methyl methacrylate copolymer.

6. The method according to claim 3, wherein the water-insoluble, acid-soluble polymer material is 2-methyl-5-vinylpyridine.methyl acrylate.methacrylic acid copolymer, poly-vinylacetacetal.diethylaminoacetate, dimethylaminoethyl methacrylate.methyl acrylate copolymer or cellulose.acetate.N,N-di-n-butylamino.-hydroxypropyl ether.

7. The method according to claim 4, 5, 6 or 3 wherein the particles of the pharmaceutically active compound containing an organic acid are used, and said organic acid is hydroxy-lower alkane-dicarboxylic acid, hydroxy-lower alkane-tricarboxylic acid, lower alkane-dicarboxylic acid or lower alkene-dicarboxylic acid.

8. The method according to claim 7, wherein the organic acid is malic acid, tartaric acid, citric acid, malonic acid, succinic acid, maleic acid or fumaric acid.

9. The method according to claim 4, 5, 6 or 3 wherein a phase-separation-inducing agent is further added to the solution of ethylcellulose, and said phase-separation-inducing agent is polyethylene, butyl rubber, polyisobutylene or polybutadiene.

10. The method according to claim 4, 5, 6 or 3 wherein an organopolysiloxane is further added to the solution of ethylcellulose, and said organopolysiloxane is dimethylpolysiloxane or methylphenylpolysiloxane.

11. The method according to claim 4, 5, 6 or 3 wherein a surfactant is further added to the solution of ethylcellulose, and said surfactant is an ester of $C_{12-18}$ fatty acid with sorbitan, an ester of $C_{6-18}$ fatty acid with glycerin, phospholipids or calcium stearoyl-2-lactylate.

12. A method of preparing ethylcellulose microcapsules comprising:
   (i) dissolving ethylcellulose having a ethoxy content of 47 to 55 w/w % in cyclohexane to form a solution,
   (ii) dispersing particles of a pharmaceutically active compound, having a particle size of 30–1000 microns, in said solution to form a dispersion,
   (iii) cooling said dispersion until coating walls, having a viscosity of 0.1 to 50 P, are formed on and around said particles of said pharmaceutically active compound,
   (iv) adding a water-insoluble, acid-soluble polymer material to said dispersion in an amount of 0.1 to 20 grams per gram of ethylcellulose,
   (v) further cooling the product of step (iv) until the resulting embryonic microcapsules shrink and become solid by solvent loss from said coating walls thereby forming microcapsules, and
   (vi) recovering the thus-formed microcapsules.

13. The method according to claim 12, wherein the water-insoluble, acid-soluble polymer material is dialkylamino-alkylcellulose, benzylaminoalkylcellulose, carboxyalkyl-(benzylamino)cellulose, dialkylaminoacetate.cellulose.acetate, cellulose.acetate.-dialkylamino.hydroxyalkyl ether, piperidyl.alkyl.hydroxyalkylcellulose, carboxyalkyl.piperidyl.starch, poly-dialkylaminoalkylstyrene, poly-vinylacetacetal.-dialkylaminoacetate, 2-(p-vinylphenyl)glycine.vinyl acetate copolymer, N-vinylglycine.styrene copolymer, a copolymer of (A) dialkylaminoalkyl methacrylate and (B) one or two alkyl methacrylates; a copolymer of (A) 2-alkyl-5-vinylpyridine, (B) alkyl acrylate or acrylonitrile and (C) methacrylic acid; a copolymer of 2-vinyl-5-alkylpyridine and styrene; or a copolymer of 2-vinylpyridine and alkyl methacrylate.

14. The method according to claim 12, wherein the water-insoluble, acid-soluble polymer material is diethylamino-methylcellulose, benzylaminomethylcellulose, carboxymethyl-(benzylamino)cellulose, diethylaminoacetate.cellulose.acetate, cellulose.acetate.N,N-di-n-butylamino.hydroxypropyl ether, piperidyl.ethyl.hydroxypropylcellulose, piperidyl.ethyl.hydroxyethylcellulose, carboxymethyl.-piperidyl.starch, poly-diethylaminomethylstyrene, poly-vinylacetacetal.diethylaminoacetate, 2-(p-vinylphenyl)glycine.vinyl acetate copolymer, N-vinylglycine.styrene copolymer, dimethylaminoethyl methacrylate.methyl methacrylate copolymer, butyl methacrylate.2-dimethylaminoethyl methacrylate.methyl methacrylate copolymer, 2-methyl-5-vinylpyridine.-methyl acrylate.methacrylic acid copolymer, 2-methyl-5-vinylpyridine.acrylonitrile.methacrylic acid copolymer, 2-vinyl-5-ethylpyridine.styrene copolymer or 2-vinylpyridine.methyl methacrylate copolymer.

15. The method according to claim 12, wherein the water-insoluble, acid-soluble polymer material is 2-methyl-5-vinylpyridine.methyl acrylate.methacrylic acid copolymer, poly-vinylacetacetal.diethylaminoacetate, dimethylaminoethyl methacrylate.methyl acrylate copolymer or cellulose.acetate.N,N-di-n-butylamino.-hydroxypropyl ether.

16. The method according to claim 12, 13, 14 or 15 wherein the particles of the pharmaceutically active compound containing an organic acid are used, and said organic acid is hydroxy-lower alkane-dicarboxylic acid, hydroxy-lower alkane-tricarboxylic acid, lower alkane-dicarboxylic acid or lower alkene-dicarboxylic acid.

17. The method according to claim 16, wherein the organic acid is malic acid, tartaric acid, citric acid, malonic acid, succinic acid, maleic acid or fumaric acid.

18. The method according to claim 12, 13, 14 or 15 wherein a phase-separation-inducing agent is further added to the solution of ethylcellulose, and said phase-separation-inducing agent is polyethylene, butyl rubber, polyisobutylene or polybutadiene.

19. The method according to claim 12, 13, 14 or 15 wherein an organopolysiloxane is further added to the solution of ethlcellulose, and said organopolysiloxane is dimethylpolysiloxane or methylphenylpolysiloxane.

20. The method according to claim 12, 13, 14 or 15 wherein a surfactant is further added to the solution of ethylcellulose, and said surfactant is an ester of $C_{12-18}$ fatty acid with sorbitan, an ester of $C_{6-18}$ fatty acid with glycerin, phospholipids or calcium stearoyl-2-lactylate.

* * * * *